United States Patent
Sigal

(10) Patent No.: US 10,295,539 B2
(45) Date of Patent: May 21, 2019

(54) SEROLOGY ASSAYS

(75) Inventor: George Sigal, Rockville, MD (US)

(73) Assignee: MESO SCALE TECHNOLOGIES, LLC., Rockville, MD (US)

( * ) Notice: Subject to any disclaimer, the term of this patent is extended or adjusted under 35 U.S.C. 154(b) by 584 days.

(21) Appl. No.: 13/642,347

(22) PCT Filed: Apr. 18, 2011

(86) PCT No.: PCT/US2011/032853
§ 371 (c)(1),
(2), (4) Date: Oct. 19, 2012

(87) PCT Pub. No.: WO2011/133450
PCT Pub. Date: Oct. 27, 2011

(65) Prior Publication Data
US 2013/0040850 A1 Feb. 14, 2013

Related U.S. Application Data

(60) Provisional application No. 61/342,747, filed on Apr. 19, 2010.

(51) Int. Cl.
*G01N 33/569* (2006.01)
*G01N 33/543* (2006.01)
*G01N 33/566* (2006.01)

(52) U.S. Cl.
CPC . *G01N 33/56983* (2013.01); *G01N 33/54313* (2013.01); *G01N 33/566* (2013.01); *G01N 2500/02* (2013.01)

(58) Field of Classification Search
None
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquish et al. | |
| 5,208,535 A | 5/1993 | Nakayama et al. | |
| 5,637,201 A | 6/1997 | Raguse et al. | |
| 5,807,522 A | 9/1998 | Brown et al. | |
| 6,066,448 A * | 5/2000 | Wohlstadter | G01N 21/66 204/400 |
| 6,110,426 A | 8/2000 | Shalon et al. | |
| 6,406,698 B1 * | 6/2002 | Svehang | C07K 14/47 424/1.13 |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0189311 A1 | 9/2004 | Glezer et al. | |
| 2005/0052646 A1 | 3/2005 | Wohlstadter et al. | |
| 2005/0142033 A1 | 6/2005 | Glezer et al. | |
| 2006/0068499 A1 * | 3/2006 | Wohlstadter | B01L 3/5027 436/172 |
| 2006/0127938 A1 * | 6/2006 | Salamone et al. | 435/6 |
| 2008/0299587 A1 | 12/2008 | Durbin | |
| 2009/0220941 A1 * | 9/2009 | Arad | A61K 31/739 435/5 |
| 2010/0120020 A1 | 5/2010 | Kachurin et al. | |

FOREIGN PATENT DOCUMENTS

WO WO 99/26067 5/1999

OTHER PUBLICATIONS

Blixt et al., "Printed covalent glycan array for ligand profiling of diverse glycan binding proteins", PNAS, vol. 101, No. 49, p. 17033-17038 + Supplementary Material p. 1-3 (2004).*
Mohammed A.R. et al., "Lyophilisation and Sterilisation of Liposomal Vaccines to Produce Stable and Sterile Products", *Methods* 40:30-38 (2006).
Török Z. et al., "Preservation of Trehalose-Loaded Red Blood Cells by Lyophilization", *Cell Preservation Technology* 3(2):96-111 (Nov. 2, 2005).
Kaufmann S. et al., "Cell Adhesion onto Highly Curved Surfaces: One-Step Immobilization of Human Erythrocyte Membranes on Silica Beads", *Chemphyschem* 4(7):699-704 (Jul. 14, 2003).
Palmgren M.G. et al., "Sealed Inside-Out and Right-Side-Out Plasma Membrane Vesicles", *Plant Physiol.* 92:871-880 (1990).
Walsh F.S. et al., "Preparation of Inside-Out Vesicles of Pig Lymphocyte Plasma Membrane", *Biochemistry* 15(16):3557-3563 (1976).
Steck TL et al., "Inside-Out Red Cell Membrane Vesicles: Preparation and Purification", *Science* 168:255-257 (1970).
Szöke C. et al., "Binding of Extracellular Matrix Proteins to the Surface of Anaerobic Bacteria", *J. Med. Microbiol.* 45:338-343 (1996).
Delehanty J.B., "Printing Functional Protein Microarrays Using Piezoelectric Capillaries", *Methods in Molecular Biology* 264:135-143 (2004).
Lue R.Y.P. et al., "Site-Specific Immobilization of Biotinylated Proteins for Protein Microarray Analysis", *Methods in Molecular Biology* 264:85-100 (2004).
Lovett R.A., "Toxicogenomics: Toxicologists Brace for Genomics Revolution", *Science* 289(5479):536-537 (2000).
Berns A., "Gene Expression in Diagnosis", *Cancer* 403:491-492 (Feb. 3, 2000).
Walt D.R., "Molecular Biology: Bead-Based Fiber-Optic Arrays", *Science* 287(5452):451-452 (Jan. 21, 2000).
Vignali D.A.A., "Multiplexed Particle-Based Flow Cytometric Assays", *Journal of Immunological Methods* 243:243-255 (2000).
Park M.K. et al., "A Latex Bead-Based Flow Cytometric Immunoassay Capable of Simultaneous Typing of Multiple Pneumococcal Serotypes (Multibead Assay)", *Clinical and Diagnostic Laboratory Immunology* 7(3):486-489 (May 2000).

(Continued)

*Primary Examiner* — Shanon A. Foley
*Assistant Examiner* — Myron G Hill
(74) *Attorney, Agent, or Firm* — Scully, Scott, Murphy & Presser, P.C.

(57) ABSTRACT

The invention provides methods and kits for measuring the ability of a test sample to inhibit the binding of a receptor expressed by a pathogen to a host cell ligand of the pathogen.

28 Claims, 2 Drawing Sheets

(56) References Cited

OTHER PUBLICATIONS

Chen R. et al., "Simultaneous Quantification of Six Human Cytokines in a Single Sample Using Microparticle-Based Flow Cytometric Technology", *Clinical Chemistry* 45(9):1693-1694 (1999).

Matrosovich M.N. et al., "Probing of the Receptor-Binding Sites of the H1 and H3 Influenza A and Influenza B Virus Hemagglutinins by Synthetic and Natural Sialosides", *Virology* 196:111-121 (1993).

Choi S-K, "Monomeric Inhibitors of Influenza Neuraminidase Enhance the Hemagglutination Inhibition Activities of Polyacrylamides Presenting Multiple C-Sialoside Groups", *Chemistry & Biology* 3(2):97-104 (Feb. 1996).
International Search Report dated Dec. 26, 2011 received from the Korean Intellectual Property Office from related International Application No. PCT/US2011/032853.

* cited by examiner

SEROLOGY ASSAYS

CROSS-REFERENCE TO RELATED APPLICATIONS

This application claims the benefit of U.S. Provisional Application No. 61/342,747 filed on Apr. 19, 2010, the entire contents of which are incorporated herein by reference.

FIELD OF THE INVENTION

This application relates to methods and kits for conducting serology assays. The invention uses arrays of viral receptors to provide a more robust and scalable alternative to the hemagglutination inhibition (HAI) and microneutralization assays that are typically used to evaluate antibody responses to viral infection or vaccination.

BACKGROUND OF THE INVENTION

The ability to identify influenza-specific antibodies in an individual's blood is important for a variety of reasons: i) serology testing is used in epidemiological studies to determine the extent of infection in the population and to characterize the diversity of influenza strains; ii) serological testing of blood from people receiving vaccines is used to assess the efficacy of vaccines; iii) serological testing is also used to determine if new vaccine strains can be neutralized by the antibodies generated with old vaccine formulations or if the viruses used in the vaccine formulations need to be updated to new strains.

In a serology assay based on conventional ELISA analysis, disease-specific antibodies in a patient sample bind to immobilized antigens. Antibody binding is detected with a labeled anti-species antibody. This "direct binding" format, while simple to carry out, is often not used for influenza serology because i) conventional direct binding approaches may not differentiate antibody responses to a recent infection from antibody responses to previous influenza infection; and ii) a response in a direct binding assay may not be indicative of the ability of an antibody to prevent influenza infection. To circumvent these problems, most influenza serology measurements are carried out using techniques that focus on identifying antibodies (termed "neutralizing antibodies") that bind to hemagglutinin or neuraminidase active sites and prevent influenza from binding and/or infecting host cells. Because these active sites change over time as new strains evolve, neutralizing antibodies tend to be more indicative of recent infections. In vaccine studies, the generation of neutralizing antibodies is also more indicative of vaccine efficacy.

During the infection process, influenza viruses bind to sialic acid groups on host cells through a sialic acid receptor, the viral hemagglutinin protein. Hemagglutination inhibition (HAI) assays measure the ability of antibodies to bind virus hemagglutinin proteins and prevent the binding of virus to red blood cells. The assay end point is visual. In the absence of antibody, the binding of the virus to red blood cells causes the formation of a red gel-like aggregate (hemagglutination) that fills the test well/tube. In the presence of a sufficient neutralizing antibody, hemagglutination is prevented and the red blood cells settle to a small pellet at the bottom of the test well/tube. Microneutralization assays involve mixing virus with the test antibody sample and combining that mixture with a virus-susceptible cell line. In the absence of antibody, the cells become infected while in the presence of sufficient neutralizing antibody the cells remain uninfected.

Both the HAI and microneutralization assays require fresh living cells that must be collected or grown just in time for the assay. These approaches are cumbersome and can lead to significant day-to-day variability in results. Because the end points are binary (hemagglutinated or not; infected or not), a large number of dilutions must be run for each sample to identify the concentration of a sample needed to cause neutralization. The formats are also inherently singleplex. To test the ability of a sample to neutralize multiple different virus strains requires multiple independent measurements.

SUMMARY OF THE INVENTION

Therefore, the present invention provides a method for measuring the ability of a sample to inhibit the binding of a receptor expressed by a pathogen to a host cell ligand of the pathogen, the method comprising (a) contacting a first surface comprising the receptor immobilized thereto with (i) the sample; and (ii) a particle reagent comprising the ligand; and (b) measuring the amount of the particle reagent bound to the first surface. In one embodiment, the method further includes the step of incubating the first surface to allow an amount of the particle reagent to bind to the surface. In an alternative embodiment, the invention provides a method for measuring the ability of a sample to inhibit the binding of a receptor expressed by a pathogen to a host cell ligand of the pathogen, the method comprising (a) contacting a first surface comprising a receptor immobilized thereto with: (i) the sample; and (ii) a particle reagent comprising ligand, and (b) measuring the amount of the ligand bound to the first surface. In one embodiment, the receptor is a sialic acid receptor and the ligand is sialic acid.

The contacting step (step (a)) may include (x) incubating the sample and the first surface; and (y) adding the particle reagent to the mixture formed in step (x). Alternatively, the first surface is contacted with a mixture comprising the sample and the particle reagent. In addition, the method may also include washing the mixture formed in step (x) prior to adding the particle reagent.

In one embodiment, the sample comprises an antibody and the measuring step further comprises determining the ability of the antibody to inhibit the binding of the receptor to the ligand. Moreover, the first surface may comprise a plurality of different receptors/ligands and the measuring step comprises measuring the amount of particle reagent bound to each of the different receptors/ligands.

Still further, the method may comprise repeating the method with one or more control samples having known inhibitory abilities and comparing the concentration of bound particle reagent measured with the sample to the concentration of bound particle reagent measured for the one or more control samples to determine the relative inhibitory ability of the sample. For example, the one or more control samples include a negative control sample having no inhibitory component; and/or the one or more control samples include a positive control sample having a defined concentration of an inhibitory component.

In one embodiment, the first surface is positioned within a well of a multi-well assay plate and the sample is measured in the well and optionally, one or more control sample are measured in one or more additional wells of the multi-well assay plate.

The invention also provides a kit for measuring the ability of a sample to inhibit the binding of a receptor expressed by a pathogen to a host cell ligand of the pathogen, the kit comprising, in one or more containers, vessels or compartments: (a) a first surface comprising the receptor immobilized thereto; and (b) a particle reagent comprising the ligand. Alternatively, the invention provides a kit for measuring the ability of a sample to inhibit the binding of a receptor expressed by a pathogen to a host cell ligand of the pathogen, the kit comprising, in one or more containers, vessels or compartments: (a) a first surface comprising the receptor immobilized thereto; and (b) the particle reagent comprising the ligand. In one embodiment, the receptor is a sialic acid receptor and the ligand is sialic acid.

The first surface may comprise a patterned array of receptors immobilized thereto. The array of receptors may be different strains, subtypes, types, and/or organisms. The kit may also include one or more control samples having known inhibitory abilities, and/or a negative control sample having no inhibitory component. One or more control samples may include a positive control sample having a defined concentration of an inhibitory component.

One or more of the components used in the method and/or present in a kit of the invention may be contained within an assay cartridge and/or a multi-well plate. In addition, one or more of the components are provided in the kit as a reconstitutable dry reagent. In this embodiment, the dry reagent and the first surface are located in a well of a multi-well plate and the dry reagent is (i) free standing; (ii) located in a surface of the first surface that does not overlap with the receptor; or (iii) located on a ledge within the well.

The receptor may be a sialic acid receptor from a virus selected from the group consisting of human coronavirus, bovine coronavirus, mouse hepatitis virus, equine rhinitis A, Influenza A virus, Influenza B virus, and Influenza C virus, Newcastle Disease Virus, murine parvovirus minute virus, reovirus, rotavirus host cell invasion, bluetongue virus, bovine adenovirus serotype 3. In a preferred embodiment, the virus is an Influenza virus. The measuring step may be used to diagnose if a patient is infected by the pathogen, and/or to determine the efficacy of a vaccination protocol for the treatment or prevention of an infection characterized by the presence of the pathogen.

Moreover, the particle reagent may comprise a biological reagent selected from the group consisting of red blood cells, red blood cell vesicles, red blood cell ghosts, membrane fragments, membrane vesicles, proteins, and combinations thereof. In one specific embodiment, biological reagent is mucin. The particle reagent may be cross-linked. In addition, the particle reagent may comprise a coating comprising the biological reagent, and the particle reagent is selected from the group consisting of colloids, beads, and combinations thereof. For example, the particle reagent is comprised of a substance selected from the group consisting of polystyrene, polyacrylamide, polypropylene, and latex particles, silica, alumina, carbon fibrils, and combinations thereof. The particle reagent may be magnetic, conductive and/or semiconductive material. In one specific embodiment, the particle reagent comprises colloidal gold particles. The receptor may be provided in a form selected from the group consisting of whole virus, virus-like particles, purified hemagglutinins, recombinant hemagglutinins, purified neuraminidases, recombinant neuraminidases, membrane fragments, membrane vesicles, and combinations thereof.

The measuring step may comprise measuring the amount of a detectable label attached to the particle reagent, indirectly or directly, e.g., via a labeled secondary binding reagent. In one embodiment, the secondary binding reagent is an antibody. The measuring step may include measuring a property selected from the group consisting of optical absorbance, fluorescence, phosphorescence, chemiluminescence, light scattering, magnetism, and combinations thereof. In one specific embodiment, the detectable label is an electrochemiluminescence (ECL) label and the measuring step comprises measuring an ECL signal. The method optionally comprises correlating the signal with the inhibitory abilities of the sample. For example, the first surface may be an electrode and the measuring step further comprises applying a voltage waveform to the electrode to generate ECL.

DETAILED DESCRIPTION OF THE INVENTION

Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The articles "a" and "an" are used herein to refer to one or to more than one (i.e., to at least one) of the grammatical object of the article. By way of example, "an element" means one element or more than one element.

The invention provides methods and kits for measuring the ability of a test sample to inhibit the binding of a receptor expressed by a pathogen to a host cell ligand of the pathogen. In one embodiment, the method includes (a) contacting a surface including a receptor immobilized thereto with the test sample and a particle reagent comprising the ligand; and (b) measuring the amount of the particle reagent bound to the first surface. Alternatively, the surface may have the ligand immobilized thereto and the method includes contacting the surface with a particle reagent comprising the receptor. Accordingly, the invention provides a kit including, in one or more compartments, vessels, or containers, (a) a surface including a receptor immobilized thereto; and (b) a particle reagent comprising the ligand; or the kit includes (a) a surface including a ligand immobilized thereto; and (b) a receptor. In a preferred embodiment, the receptor is a sialic acid receptor and the ligand is sialic acid.

Figures 1A, 1B:
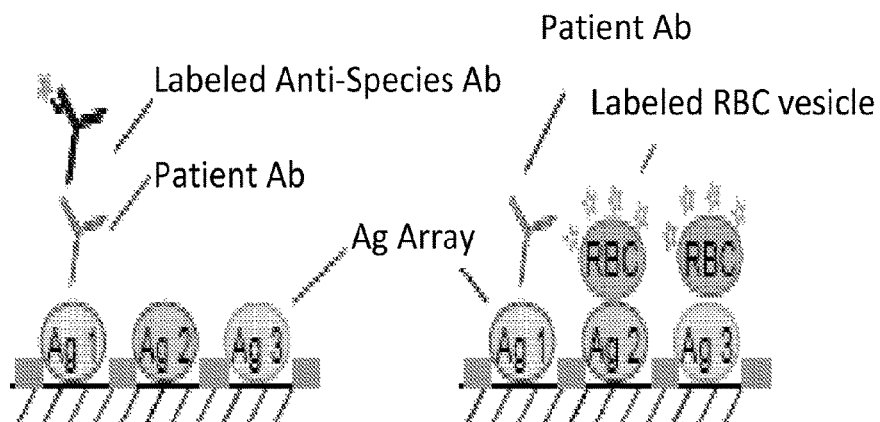
FIGS. 1(a)-(c) are schematic representations showing a viral antigen array (panel (c)) and the use of such an array in a direct serology assay in which the binding of patient antibodies to antigens on the array is detected with a labeled anti-species detection antibody (panel (a)) and in a viral receptor neutralization assay in which the presence of neutralizing patient antibodies against antigen 1 on the array prevents binding of sialic acid receptors on the antigen to labeled red blood cell (RBC) vesicles (panel (b)).
Figure 1C:
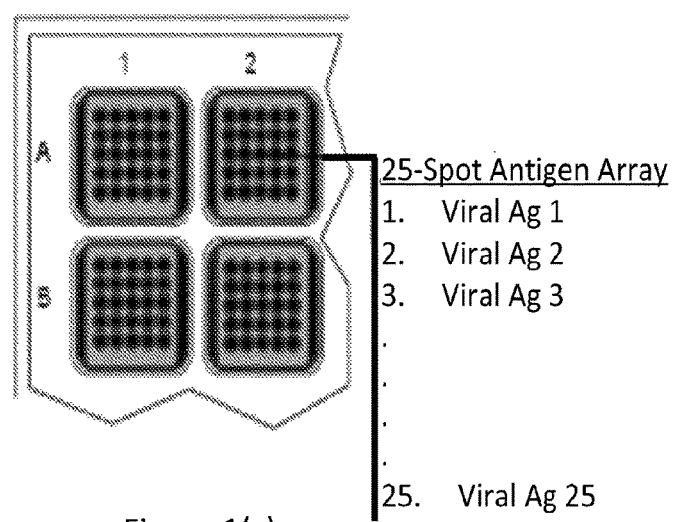
Figure 2B:
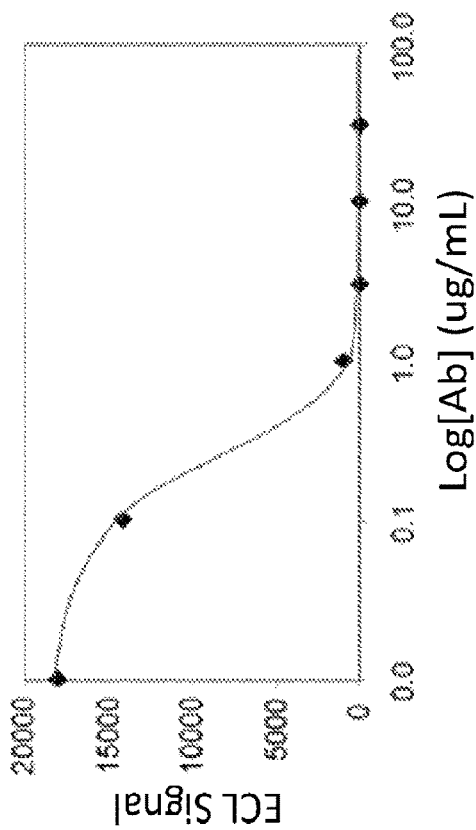
FIGS. 2(a)-(b) show an assay configured according to one embodiment of the present invention (panel (a)) and the results obtained from this assay (panel (b)).
Figure 2A:
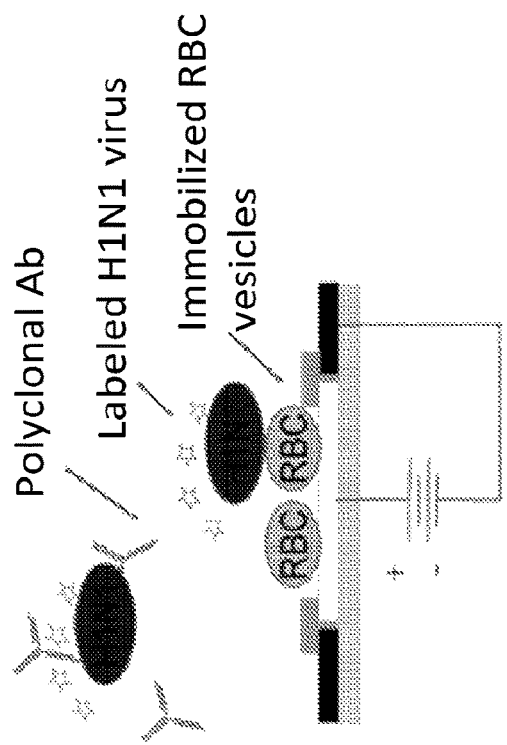

The invention includes multiplexed formats in which the sample and a particle reagent comprising a ligand contact a plurality of binding domains including immobilized receptors on one or more surfaces, the different binding domains presenting different receptors for that ligand (for example, from different organisms or from different types, subtypes or strains of an organism). The invention also includes multiplexed formats in which the sample and a particle reagent comprising a receptor from a pathogen are contacted with a plurality of binding domains including immobilized ligands on one or more surfaces, the different binding domains presenting different ligands for that receptor (e.g., ligands, such as sialic acid, from different host animal species/strains and/or from different tissue types within a species/strain) One embodiment of the invention is illustrated in FIG. 1. FIG. 1(c) depicts an array of receptors from pathogens immobilized to a solid surface (the figure depicts an array positioned on the bottom of a well of a multi-well plate). The array is contacted with a sample comprising inhibitors of the binding of viral receptors to their host cell ligands (in this specific example, the inhibitors are depicted as antibodies). The array is also contacted with a particle reagent comprising the host cell ligand (in this specific example, the particle reagent is a red blood cell). The result of these steps is illustrated in FIG. 1(b). In this specific example, the sample contains a neutralizing antibody that binds to antigen 1 in the array and inhibits the binding of the particle reagent to the array element containing that antigen. Measurement of the amount of particle reagent bound to a specific array element (directly, through a detectable label on the particle reagent and/or through a secondary reagent that binds the particle reagent) is indicative of the ability of the sample to prevent the binding of the receptor in that array element to its host cell ligand. The assay format is also applicable to singleplex formats measuring binding to a single viral receptor. In addition, the same format may be applied to multiplexed assays employing array elements on separate surfaces, such as multiplexed bead array formats (described in more detail below). To contrast the receptor neutralization format to the direct serology format, FIG. 1 also illustrates the use of the same antigen array in a direct serology format employing a labeled anti-species antibody as the detection reagent (FIG. 1(a)).

Because the receptor neutralization assay format measures a functional activity that is specific to the receptor, the presence of other proteins in the preparation does not interfere with the measurement and high purity levels are not critical and, e.g., the receptor can be provided in the form of a crude preparation of the pathogen of interest. In this format, the receptor surface is incubated with particles that present multiple copies of a ligand of the receptor. The presence of multiple ligands per particle provides a high avidity interaction to the surface even if the individual receptor-ligand interactions are low affinity. In one embodiment, the surface is contacted with a mixture comprising the sample and a particle reagent, incubated, and the concentration of the particle reagent bound to the surface is measured. Alternatively, the surface is first incubated with the sample, the particle reagent is subsequently added and thereafter ligand-receptor binding is measured. Optionally, the method may include a washing step, e.g., in which the surface is washed prior to contacting the surface with the particle reagent/receptor, and/or prior to the measurement step. One or more components of the assay may be provided as reconstitutable dry reagents. In specific examples of such an embodiment, a dry reagent may be located within the same container as the solid surface (e.g., within a well of a multi-well plate) as a free standing component such as a dry reagent bead, the dry reagent may be located on a supplemental surface of the solid surface that does not overlap with a binding domain on said first surface and/or the dry reagent may be located on a ledge within the container. If one or more components are provided in dry form, the addition of sample or other reagents to the surface can be used to reconstitute the dry reagent for use in the assay.

In one embodiment, the sample comprises neutralizing antibodies and the measuring step further comprises determining the ability of the neutralizing antibodies to inhibit the binding of the receptor to the ligand. The method may also include repeating the method with one or more control samples having known inhibitory activities and comparing the concentration of bound particle reagent measured with the sample to the concentration of bound particle reagent measured for one or more control samples to determine the relative inhibitory ability of the sample compared to a control. For example, the method may include (a) an analysis of a negative control sample having no inhibitory component; and/or (b) an analysis of a positive control sample having a defined concentration of an inhibitory component.

In multiplexed methods of the invention, the assay may include testing the sample with internal negative and/or positive control receptors. For example, an array of receptors from pathogens of interest may also include a negative control array element that does not bind the ligand or particle reagent. This array element should provide a low assay signal regardless of the sample. The array may also include a positive control array element that binds the ligand or particle reagent through an interaction that should not be affected by antibodies against the pathogen of interest. For example the positive array element could be a receptor against the ligand or another component of the particle reagent that is not derived from the pathogen of interest. Examples of such receptors for influenza serology assays include antibodies that bind components of the particle reagent (e.g. antibodies that bind to red blood cells when the particle reagent is derived from red blood cells) or sialic acid receptors that are not derived from influenza (such as plant lectins or hemagglutinins from non-influenza pathogens). The positive array element should provide a positive assay signal that should not be affected by antibodies against the pathogen of interest. Methods employing the internal control receptors may include measuring the amount of particle reagent bound to the surfaces/array elements comprising the control receptors and determining if the amounts are within a pre-specified acceptable range.

The assay may be used to diagnose if a patient is infected by a pathogen or to determine the efficacy of a vaccination protocol used for the treatment or prevention of an infection characterized by the presence of a pathogen. In one specific example, samples (e.g., sera, plasma, blood and/or purified antibodies) from patients given a test vaccine are tested according to the methods of the invention for the ability of antibodies in the samples to prevent a ligand (such as sialic acid) from binding to multiple different strains of a pathogen (such as different strains of influenza). Such an approach may be used to ensure that a vaccine provides protection against the diversity of strains to which vaccinated individuals may be exposed. This approach may also be used to test samples from vaccinated individuals or samples from individuals that have been exposed in the past to pathogens, to determine if the antibodies generated against these vaccines or older pathogens are useful in neutralizing one or more newly emerging strains of the pathogen and also to determine whether there is a need to change vaccine formulations to address genetic changes in the pathogen. Preferably, these approaches are carried out in a multiplexed format using the multiplexed methods and kits of the invention.

In another example, samples from individuals (which may have been selected based on known exposure to a pathogen) are tested for their ability to inhibit the receptor from multiple strains of the pathogen to provide an epidemiological characterization of the circulating strains of the pathogen in a population.

In another example, a particle reagent comprising a receptor from a pathogen is contacted with one or more surfaces comprising different ligands (preferably, in a multiplexed format of the invention) and the binding of the particle reagent to the ligands is measured to determine the ligand specificity of the pathogen receptor. For example, different sialic acid structures (which may be synthetically created or isolated from different animal species/strains or different tissue types from an animal species/strain) are tested to determine the sialic acid specificity of an influenza virus hemagglutinin.

In a preferred embodiment, the receptors are sialic acid receptors that the corresponding ligand is sialic acid. Sialic acid is a generic term for the N- or O-substituted derivatives of neuraminic acid, a nine-carbon monosaccharide. Sialic acids are found widely distributed in animal tissues and in bacteria, especially in glycoproteins and gangliosides. The amino group bears either an acetyl or a glycolyl group. Sialic acid structure may differ from one strain, type, subtype and/or organism to another.

Sialic acid receptors may be the same or different and the assay may involve measuring a binding interaction between sialic acid moieties different sialic acid receptors. In certain embodiments, the receptor is a sialic acid receptor from a virus selected from the group consisting of human coronavirus, bovine coronavirus, mouse hepatitis virus, equine rhinitis A, Influenza A virus, Influenza B virus, and Influenza C virus, Newcastle Disease Virus, murine parvovirus minute virus, reovirus, rotavirus host cell invasion, bluetongue virus, bovine adenovirus serotype 3. In a specific embodiment, the virus is an Influenza virus. The receptor may be presented as a whole virus, virus-like particles, purified hemagglutinins, recombinant hemagglutinins, purified neuraminidases, recombinant neuraminidases, membrane fragments, membrane vesicles, and combinations thereof.

For hemagglutinin assays, one convenient source of sialic coated particles is red blood cells. Optionally, to provide stable reagents that can be prepared in large quantities and stored for later use, it may be preferable to use red blood cell ghosts, membrane fragments or vesicles which may, optionally, be cross-linked. Alternatively, cells, membrane fragments or vesicles from other cell types may be used. In one embodiment cells from or derived from the epithelia of the respiratory or gastro-intestinal tracts are used because these cells also tend to display sialic acids. The predominant sialic acid structure can be varied by selecting cells from different locations in the respiratory or gastro-intestinal tracts. One skilled in the art will be able to select cells that bind the viruses of interest and/or screen through cell type to identify cells with appropriate binding characteristics. Moreover, it is known that red blood cells from different species may have different binding affinities for viral particles. Therefore, it may be beneficial to screen through cells from different species to find cells with optimal binding characteristics. In another approach, proteins presenting multiple sialic acids (e.g., fetuins, mucins and α-acid glycoproteins) are used instead of particles or are coated on particles to provide the particle reagent. In yet another approach, synthetic sialic acids or conjugates of synthetic sialic acids and other components (such as lipids or synthetic or biological polymers including proteins, polysacharrides) are used and are coated or chemically coupled to particles to prepare the particle reagents.

The particle reagent comprising a host cell ligand may include a biological reagent selected from the group consisting of red blood cells, red blood cell vesicles, red blood cell ghosts, membrane fragments, membrane vesicles, proteins, and combinations thereof. In one embodiment, the particle reagent is cross-linked. The particle reagent itself may be a biological material, e.g., red blood cells, red blood cell vesicles, red blood cell ghosts, membrane fragments, membrane vesicles, proteins, and combinations thereof, or it may be comprised of another, e.g., synthetic material, that may be coated with a biological reagent. The particle itself may consist of colloids, beads, and combinations thereof. In one embodiment, the particle reagent is comprised of a substance selected from the group consisting of polystyrene, polyacrylamide, polypropylene, and latex particles, silica, alumina, carbon fibrils, and combinations thereof. The particle may be magnetic, conductive and/or semiconductive. In one specific embodiment, the particle reagent consists of colloidal gold particles. Where the method employs a ligand immobilized on a surface, the immobilized component may be formed by immobilizing a particle reagent comprising the ligand as described above.

In one embodiment the particle is between 10 nm and 1 mm in diameter. In another embodiment, the particle is between 10 nm and 0.02 mm in diameter. In another embodiment, the particle is between 40 nm and 1000 nm in diameter.

In one embodiment, the particle is a labeled cell, cell ghost or a small unilamellar vesicle (SUV) prepared from a cell, for example, from a red blood cell. Such particles may be provided as stable or frozen preparations. For a discussion of the preparation of stable frozen or lyophilized vesicle preparations, see, e.g., Mohammed A R et al., Methods, 2006, 40, 30-38. For a discussion of approaches to stabilizing red blood cells for storage, see, e.g., Török, Z. et al., Cell Preservation Technology, 2005, 3: 96-111.

In one embodiment, the particle may be coated with a biological membrane which is displayed on the particle. Such membrane coated particles may be prepared by incubating particles with membranes (e.g., cells, membrane fragment and membrane vesicles). The approach may be used with metal particles, high surface area particles, e.g., silica or other particles with oxide-based surfaces, and particles with a hydrophobic surface. In a preferred embodiment, the particle is a silica particle. During this coating process, the membrane orientation is reversed. Incubating red blood cell ghosts with silica particles, therefore, leads to silica particles presenting the cytoplasmic side of the red blood cell membranes (Kaufmann S et al., Chem Phys Chem, 2003, 4, 699-704).

The invention includes a method for coating particles with membranes so as to display the outside surface of a cell by incubating particles (e.g., silica particles) with inside-out membranes, i.e., any vesicle formed from disrupted cell or other membranes in which the face of the membrane that was originally on the outside surface is now on the inside. The invention also includes such particles and their use in the assays of the invention. Inside out vesicles for use in the method can be formed using established methods such as those described in Palmgren et al., Plant Physiol, 1990, 92, 871-880 or Walsh et al., Biochemistry, 1976, 15, 3557-63. Specific methods for preparing inside out red blood cell ghosts for use in forming coated particles presenting the outer surface of red blood cell particles are described, e.g., in Steck T L et al., Science, 1970, 168, 255-257).

In an alternative embodiment, vesicles or undefined or random membrane orientation are used to coat particles, such that the particles present both internal and external membrane proteins. Such vesicles include, but are not limited to, vesicles prepared by sonication or by removing detergent from detergent from detergent-solubilized membranes. In one example, red blood cell SUVs presenting both internal and external membrane proteins (e.g., SUVs prepared by sonication) are used as the membrane protein source to create particles presenting a random distribution of internal and external red blood cell membrane proteins.

In another alternate embodiment, cell or membrane lysates solubilized in detergent are covalently coupled to particles. In one example, the coupling is by using standard EDC coupling protocols to attach components of the lysates to carboxyl modified latex particles, although other know functionalized particles and coupling chemistries may be used. Where maintaining protein structure is critical, a non-denaturing detergent is, preferably, used. For secondary structure independent binding groups such as sugars, denaturing or non-denaturing detergents may be used. Useful detergents include non-ionic detergents such as Triton X-100. In one specific example, red blood cell surface proteins are coupled to a particle.

In another alternate embodiment, labeled soluble proteins are used in the assay methods of the invention instead of the labeled particles. In one example, soluble sialic acid containing proteins (e.g., fetuins, mucins or α-acid glycoproteins) are labeled and used in monomeric form. The soluble proteins may also be aggregated by chemical cross-linking (e.g., using established methods such gluteraldehyde cross-linking) to form larger aggregates with higher avidity. Alternatively, the soluble proteins (e.g., the sialic acid containing proteins as described above) may be adsorbed or covalently linked to particles. By way of example, the coating of particles with mucin and fetuin by adsorption to unmodified latex particles or by covalent coupling to carboxy-modified latex particles is described in Szoke et al., J. Med. Microbiol., 1996, 45, 338-343, as is the use of these particles in latex-agglutination assays.

In one preferred embodiment, the invention includes immobilization of a material, e.g., a receptor or particle reagent, onto one or more assay electrodes. Such electrodes may be incorporated into a variety of different assay modules suitable for carrying out assays, e.g., assay plates, cassettes, cartridges, devices, etc. Preferably, the electrode is incorporated in the wells of a multi-well assay plate. The assay region or module (e.g., a given well of a multi-well plate) may also comprise additional electrodes. Preferably at least one electrode in an assay region or module (or a well of a multi-well plate) is suitable for use as a working electrode in an electrode induced luminescence assay, at least one electrode is suitable for use as counter electrode in an electrode induced luminescence assay. Optionally, there is at least one electrode that is suitable for use as a reference electrode (e.g., in a three electrode electrochemical system). Preferably, no reference electrode is included.

The receptors or particles can be immobilized on a surface via a variety of interactions including non-specific adsorption (e.g., via non-specific ionic, hydrogen bonding, polar, Van der Waals and/or hydrophobic interactions), covalent bonding, and/or specific binding interactions between binding partners (e.g., ligand/receptor, antibody/hapten, nucleic acid hybridization, biotin/avidin, biotin/streptavidin, lectin/sugar, metal/ligand, etc.). Preferably, the material is immobilized directly onto the surface, more preferably without the use of an immobilization agent (e.g., a dye, trehalose, etc.). Alternatively, a receptor or particle reagent is immobilized via the binding of a receptor or particle reagent components to antibodies immobilized on the surface. In another preferred embodiment, a receptor or particle reagent is immobilized via the binding of a labeled component of the receptor or particle reagent (e.g., a biotin or hapten labeled moiety, protein or sugar) to a binding reagent (e.g., streptavidin, avidin or an antibody) immobilized on a surface. The surface may include a spacer layer between the surface and an immobilized receptor or particle reagent. Such a layer may function, e.g., as a chemical linker for holding the layer to the surface and/or as a hydrophilic spacer volume.

In some embodiments of the invention, the immobilized receptor or particle reagent are cross-linked so as to provide greater stability. Cross-links may include i) cross-links between receptor/particle components (e.g., lipids, proteins and/or sugars) and chemical moieties on the electrode surface and ii) cross links between receptor/particle components themselves. Cross-linking may be accomplished by a variety of techniques, e.g., techniques known in the arts of tissue fixing, sample preparation for microscopy, bioconjugate chemistry, affinity-labeling and the preparation of cross-linked lipid membranes. Useful cross-linking reagents include cross-linking reagents that comprise one or more functional groups capable of reacting with components of a receptor/particle layer or an electrode surface (e.g., imidoesters, active esters such as NHS esters, maleimides, α-halocarbonyls, disulfides such as pyridyldithiols, carbodiimides, arylazides, amines, thiols, carboxylates, hydrazides, aldehydes or ketones, active carbamates, glyoxals, etc.). In some applications it may be advantageous to use photo-reactive cross-linkers (such as arylazides) so as to better control the cross-linking process. Exemplary cross-linking agents include homo- and hetero-bifunctional cross-linking agents such as those sold by Pierce Chemical Co. and/or described in the 1994 Pierce Catalog and Handbook (Pierce Chemical Co., Rockford, Ill., 1994), the chapters relating to cross-linking agents hereby incorporated by reference. Lipid monolayers and bilayers may be cross-linked by chemically cross-linking lipid head-groups and/or tail groups (e.g., by including lipids with tails comprising photochemically cross-linkable groups such as alkene or alkyne groups and/or by including lipids that can span bilayer lipid membranes). See, U.S. Pat. No. 5,637,201, hereby incorporated by reference.

According to one embodiment, the assay surface is incorporated in an assay module, e.g., an electrode located in one or more wells of a multi-well plate. Suitable assay modules, including multi-well assay modules, and method of using and systems incorporating the same are set forth in U.S. application Ser. No. 10/185,274, entitled "Assay Plates, Reader Systems and Methods for Luminescence Test Measurements", filed Jun. 28, 2002 (see Sections 3, 4 and 5.1-5.6), hereby incorporated by reference. According to one preferred embodiment of the invention, an assay module or plate comprises one or more (preferably two or more, 6 or more, 24 or more, 96 or more, 384 or more, 1536 or more or 9600 or more) assay wells, assay chambers and/or assay domains (e.g., discrete locations on a module surface where an assay reaction occurs and/or where an assay signal is emitted; typically an electrode surface, preferably a working electrode surface). According to a particularly preferred embodiment, the assay plate is a multi-well assay plate having a standard well configuration (e.g., 6 well, 24 well, 96 well, 384 well, 1536 well, 6144 well or 9600 well). Alternatively, the assay surface is incorporated in an assay cartridge, e.g., as described in U.S. application Ser. No. 10/744,726, entitled "Assay Cartridges and Methods of Using the Same, filed Dec. 23, 2003, and U.S. Application Ser. No. 61/284,276, entitled "Assay Cartridges and Methods of Using the Same, filed Dec. 16, 2009, the disclosures of which are incorporated herein by reference.

The measurement of the binding interaction between a receptor/ligand may consist of measuring the amount of a detectable label attached, directly or indirectly, to the surface via a binding interaction between a ligand and a particle reagent. The measurement may also reflect the presence/absence of neutralizing antibodies in a test sample which interfere with binding between the surface immobilized particle/receptor and the free receptor/particle in solution. Receptor-ligand binding may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemiluminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte or direct visualization of particles.

Binding assays for measuring receptor/ligand interactions may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601, 4,442,204 and 5,208,535, each of which are incorporated herein by reference in their entireties.

Multiple receptor/ligand interactions may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® xMAP technology. Suitable multiplexing methods include array based binding assays using patterned arrays of immobilized receptors/particles directed associated with the pathogen. Various approaches for conducting multiplexed assays have been described (See e.g., US 20040022677; US 20050052646; US 20030207290; US 20030113713; US 20050142033; and US20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bio. (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289:536-537; Berns A, Cancer: Gene expression in diagnosis, nature (2000), 403,491-92; Walt, Molecular Biology: Bead-based Fiber-Optic Arrays, Science (2000) 287: 451-52 for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex binding assay in which 64 different bead sets of microparticles are employed, each having a uniform and distinct proportion of two dyes (Vignali, D., "Multiplexed Particle-Based Flow Cytometric Assays" J. ImmunoL Meth. (2000) 243: 243-55). A similar approach involving a set of 15 different beads of differing size and fluorescence has been disclosed as useful for simultaneous typing of multiple pneumococcal serotypes (Park, M. K et al., "A Latex Bead-Based Flow Cytometric Immunoassay Capable of Simultaneous Typing of Multiple Pneumococcal Serotypes (Multi-bead Assay)" Clin. Diag. Lab ImmunoL (2000) 7: 4869). Bishop, J E et al. have described a multiplex sandwich assay for simultaneous quantification of six human cytokines (Bishop, L E. et al., "Simultaneous Quantification of Six Human Cytokines in a Single Sample Using Microparticle-based Flow Cytometric Technology," Clin. Chem (1999) 45:1693-1694).

The method of the present invention may be conducted in a single assay chamber; such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTI-SPOT® and MULTI-ARRAY® plates and SECTOR® instruments, Mesa Scale Discovery, a division of Meso Scale Diagnostics, LLC, Gaithersburg, Md.).

According to one embodiment, the kit of the present invention includes one or more of the assay components in one or more locations on a surface and/or in a device used in an assay method, preferably in dry form. In a preferred embodiment, one or more of the components of the assay are provided in the kit as a reconstitutable dry reagent, wherein the dry reagent is free standing; or located on a supplemental surface of the first surface that does not overlap with a binding domain on the first surface. The assay components may be provided in separate containers, vessels or compartments. In one embodiment, the kit includes a container comprising one or more reagents, buffers, co-reactants, blocking agents and/or stabilizing agents.

One preferred embodiment relates to a kit for use in conducting electrode induced luminescence assays (preferably electrochemiluminescence assays) comprising an assay plate, preferably a multi-well assay plate, or an assay cartridge, including a first surface having a particle/reagent immobilized thereto, a corresponding reagent selected from a particle reagent or a receptor, and at least one assay component selected from the group consisting of at least one luminescent label (preferably electrochemiluminescent label) and at least one electrochemiluminescence coreactant). The kit may further include additional buffers and/or blocking reagents for use in the method of the present invention.

According to another embodiment, the kit is adapted for multiple assays. Preferably, the kit further comprises an additional assay reagent for use in an additional assay, the additional assay selected from the group consisting of radioactive assays, enzyme assays, chemical colorimetric assays, fluorescence assays, chemiluminescence assays and combinations thereof.

EXAMPLES

The following example is illustrative of some of the kits and methods falling within the scope of the present invention. It is, of course, not to be considered in any way limitative of the invention. Numerous changes and modification can be made with respect to the invention by one of ordinary skill in the art without undue experimentation.

Example 1. Viral Receptor Neutralization Assay

In this set of experiments, the ability of an H1 specific goat polyclonal antibody to inhibit the binding of an H1N1 virus to guinea pig red blood cell vesicles was tested. The red blood cell vesicles were made by preparing guinea pig red blood cell ghosts and sonicating the ghosts to form vesicles. H1N1 virus particles were labeled by labeling a whole virus preparation with an ECL label (SULFO-TAG™ NHS ester, Meso Scale Diagnostics, LLC, Gaithersburg, Md. 20877). When the vesicles were immobilized by passive adsorption on carbon ink electrodes, they retained the ability to bind the red blood cell vesicles via the interaction of the viral hemagglutinin with the red blood cell sialic acids. The extent of binding was measured using electrochemiluminescence. FIG. 2(*a*) shows the configuration of the assay and FIG. 2(*b*) shows the inhibition of the binding reaction that occurs when increasing amounts of a polyclonal anti-H1 antibody were introduced. In this experiment, red blood cell vesicles were immobilized and the whole virus was labeled, but the reverse orientation, i.e., immobilized virus and labeled red blood cell vesicles, will work as well.

The present invention is not to be limited in scope by the specific embodiments described herein. Indeed, various modifications of the method in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A kit for measuring a sample's inhibition of a binding of a sialic acid receptor expressed by a pathogen to a host cell ligand of said pathogen, wherein said host cell ligand is sialic acid, said kit comprising:

(a) a first container, vessel or compartment comprising a first surface comprising said sialic acid receptor immobilized thereto; and (b) a second container, vessel or compartment, the second container containing within a cavity of the second container a particle reagent comprising said sialic acid, wherein said sialic acid is bound only to the particle reagent and not the second container.

2. The kit of claim 1 wherein said first surface comprises a patterned array of receptors immobilized thereto.

3. The kit of claim 2 wherein said array of receptors is one selected from the group consisting of different strains, subtypes, types, and organisms.

4. The kit of claim 1 wherein said kit further comprises one or more control samples having known inhibitory abilities.

5. The kit of claim 4 wherein said one or more control samples include a negative control sample having no inhibitory component.

6. The kit of claim 4 wherein said one or more control samples include a positive control sample having a defined concentration of an inhibitory component.

7. The kit of claim 1 wherein said receptor is a sialic acid receptor from a virus selected from the group consisting of human coronavirus, bovine coronavirus, mouse hepatitis virus, equine rhinitis A, Influenza A virus, Influenza B virus, and Influenza C virus, Newcastle Disease Virus, murine parvovirus minute virus, reovirus, rotavirus host cell invasion, bluetongue virus, bovine adenovirus serotype 3.

8. The kit of claim 7 wherein said virus is an Influenza virus.

9. The kit of claim 1 wherein said particle reagent comprises a biological reagent selected from the group consisting of red blood cells, red blood cell vesicles, red blood cell ghosts, membrane fragments, membrane vesicles, proteins, and combinations thereof.

10. The kit of claim 1 wherein said particle reagent is cross-linked.

11. The kit of claim 10 wherein said particle reagent comprises a coating comprising said biological reagent.

12. The kit of claim 11 wherein said particle reagent is selected from the group consisting of colloids, beads, and combinations thereof.

13. The kit of claim 12 wherein said particle reagent is comprised of a substance selected from the group consisting of polystyrene, polyacrylamide, polypropylene, and latex particles, silica, alumina, carbon fibrils, and combinations thereof.

14. The kit of claim 12 wherein said particle reagent is magnetic.

15. The kit of claim 12 wherein said particle reagent is comprised of a conductive and/or semiconductive material.

16. The kit of claim 15 wherein said particle reagent comprises colloidal gold particles.

17. The kit of claim 1 wherein said receptor is provided in a form selected from the group consisting of whole virus, virus-like particles, purified hemagglutinins, recombinant hemagglutinins, purified neuraminidases, recombinant neuraminidases, membrane fragments, membrane vesicles, and combinations thereof.

18. The kit of claim 1 wherein said particle reagent comprises a detectable label.

19. The kit of claim 1 further comprising a secondary binding reagent comprising a detectable label.

20. The kit of claim 19 wherein said secondary binding reagent is an antibody.

21. The kit of claim 1 further comprising a detectable label.

22. The kit of claim 19 wherein said detectable label is an electrochemiluminescence (ECL) label.

23. The kit of claim 22 wherein said first surface comprises an electrode.

24. The kit of claim 9 wherein said biological reagent is mucin.

25. The kit of claim 1 wherein components (a)-(b) are contained within an assay cartridge.

26. The kit of claim 1 wherein components (a)-(b) are contained within a multi-well plate.

27. The kit of claim 1 wherein one or more of said components are provided in said kit as a reconstitutable dry reagent.

28. The kit of claim 27, wherein said dry reagent and said first surface are located in a well of a multi-well plate and said dry reagent is one selected from the group consisting of
  (i) free standing;
  (ii) located in a surface of said first surface that does not overlap with said receptor; and
  (iii) located on a ledge within said well.

* * * * *